United States Patent
Häpp et al.

(10) Patent No.: US 10,473,565 B2
(45) Date of Patent: Nov. 12, 2019

(54) MONITORING SYSTEM AND METHOD FOR MONITORING AND SETTING AIR PARAMETERS IN A ROOM, FUME EXTRACTION DEVICE FOR USE IN A MONITORING SYSTEM

(71) Applicant: BSH Bosch und Siemens Hausgeräte GmbH, Munich (DE)

(72) Inventors: Claudia Häpp, München (DE); Ingo Pietsch, München (DE); Sabine Thaler, München (DE)

(73) Assignee: BSH Hausgeräte GmbH, Munich (DE)

( * ) Notice: Subject to any disclaimer, the term of this patent is extended or adjusted under 35 U.S.C. 154(b) by 284 days.

(21) Appl. No.: 14/068,037

(22) Filed: Oct. 31, 2013

(65) Prior Publication Data
US 2014/0130574 A1 May 15, 2014

(30) Foreign Application Priority Data
Nov. 13, 2012 (DE) .......................... 10 2012 220 598

(51) Int. Cl.
| | |
|---|---|
| *G01N 1/22* | (2006.01) |
| *F24C 15/20* | (2006.01) |
| *F24F 11/00* | (2018.01) |
| *F24F 11/30* | (2018.01) |
| *F24F 7/00* | (2006.01) |
| *F24F 110/00* | (2018.01) |
| *F24F 11/56* | (2018.01) |
| *F24F 11/58* | (2018.01) |

(52) U.S. Cl.
CPC ........... *G01N 1/2273* (2013.01); *F24C 15/20* (2013.01); *F24F 11/0001* (2013.01); *F24F 11/30* (2018.01); *F24C 15/2021* (2013.01); *F24F 11/56* (2018.01); *F24F 11/58* (2018.01); *F24F 2007/001* (2013.01); *F24F 2110/00* (2018.01)

(58) Field of Classification Search
CPC ............. H04L 12/2803; H04L 12/2823; H04L 12/283; H04W 88/04; F24F 2011/0071; F24F 2011/0068; F24F 2007/001; F24F 11/0001; F24F 11/001; F24C 15/2021; F24C 15/20; G01N 1/2273
USPC ......................................... 126/299; 73/31.01
See application file for complete search history.

(56) References Cited

U.S. PATENT DOCUMENTS

| | | |
|---|---|---|
| 6,920,874 B1 | 7/2005 | Siegel |
| 9,217,579 B2 | 12/2015 | DiFulgentiz |
| 2002/0072356 A1* | 6/2002 | Yamashita ........ H04M 1/72533 455/420 |

(Continued)

OTHER PUBLICATIONS

European Search Report EP 13 19 0109 dated Jan. 28, 2014.
Report of Examination EP 13 19 0109 dated Sep. 27, 2018.

*Primary Examiner* — David Z Huang
*Assistant Examiner* — Truong D Phan
(74) *Attorney, Agent, or Firm* — Michael E. Tschupp; Andre Pallapies; Brandon G. Braun (57) ABSTRACT

A monitoring system for monitoring and setting at least one air parameter in a room includes at least one sensor and at least one monitoring unit, which is provided separately from the sensor. The at least one monitoring unit is connected to the sensor by a wireless communications link of a communications network. The communications network has at least one mobile terminal device on which at least a part of the monitoring unit is provided.

20 Claims, 2 Drawing Sheets

(56) References Cited

U.S. PATENT DOCUMENTS

| | | | |
|---|---|---|---|
| 2005/0224069 A1* | 10/2005 | Patil | F24C 15/2021 |
| | | | 126/299 D |
| 2007/0123391 A1* | 5/2007 | Shin | A43B 3/0005 |
| | | | 482/8 |
| 2011/0190580 A1* | 8/2011 | Bennett | A61B 1/00016 |
| | | | 600/109 |
| 2012/0064923 A1 | 3/2012 | Imes et al. | |
| 2012/0064951 A1* | 3/2012 | Agevik | G06F 3/0346 |
| | | | 455/569.1 |
| 2012/0158213 A1* | 6/2012 | Talty | B60R 25/24 |
| | | | 701/2 |
| 2012/0310547 A1* | 12/2012 | Cristoforo | G08B 21/14 |
| | | | 702/24 |
| 2013/0169443 A1* | 7/2013 | Schechter | G08B 21/00 |
| | | | 340/584 |

\* cited by examiner

Fig. 3

MONITORING SYSTEM AND METHOD FOR MONITORING AND SETTING AIR PARAMETERS IN A ROOM, FUME EXTRACTION DEVICE FOR USE IN A MONITORING SYSTEM

BACKGROUND OF THE INVENTION

The invention relates to a monitoring system and a method for monitoring and setting air parameters in a room as well as to a fume extraction device for use in such a monitoring system and/or method.

It is known to employ sensors for monitoring conditions in buildings, in particular for detecting hazardous situations. For example, temperature sensors for surface mounting are often also known in combination with hygrometers. In addition there are certain fire gas or smoke gas detectors which sound an alarm if the concentration of carbon monoxide, carbon dioxide or other combustion gases in a room exceeds a specific value and as a consequence there exists the risk of a fire or, as the case may be, poisoning by smoke gas.

A disadvantage of these known sensors is that on the one hand they can only be used in a locally limited space and on the other hand they generally are only able to communicate with a single component specifically connected to the sensor in order to trigger an alarm, for example.

BRIEF SUMMARY OF THE INVENTION

It is therefore an object of the present invention to provide a solution by means of which the air parameters of a room in a building can be determined and set in a flexible manner.

The invention is based on the knowledge that this object can be achieved through provision of at least one sensor which is able to communicate on a flexible basis with a monitoring unit and whose data can be processed further in an intelligent manner.

According to a first aspect of the invention, the object is achieved by means of a monitoring system for monitoring and setting at least one air parameter in a room. The monitoring system is characterized in that it comprises at least one sensor, at least one monitoring unit which is provided separately from the sensor and is connected to the sensor via a wireless communications link of a communications network, and at least one mobile terminal device of the communications network, on which device at least a part of the monitoring unit is provided.

A monitoring system, within the meaning of the invention, is understood to mean a system whose components in combination serve to enable air parameters in a room to be monitored and set. By air parameters, according to the invention, are to be understood parameters which provide information about the air quality. In this context both parameters relating to the composition of the air and parameters relating to the temperature of the air are referred to as air parameters. With regard to the parameters relating to the composition of the air, both qualitative and quantitative parameters are understood to mean air parameters. The parameters relating to the composition of the air can be in particular the relative humidity of the air and/or the content in terms of solid or gaseous substances. For example, the content and where applicable the type of pollen in the air can therefore be used as air parameters according to the invention. Furthermore, the content of, for example, carbon monoxide, carbon dioxide, sulfur dioxide and/or oxides of nitrogen can be used as air parameters. Different air parameters can be acquired by way of different sensors, though it is also possible to acquire more than one air parameter by way of a single sensor. According to the invention, at least one air parameter is monitored and set, although it is preferred for more than one, in particular at least two, air parameters to be set. Reference is made hereinbelow essentially to a plurality of air parameters, without the invention being limited thereto. Embodiments relating to a plurality of air parameters are also valid—where applicable—for an individual air parameter.

According to the invention, the acquisition or detection of the air parameters or, as the case may be, of corresponding sensor signals is referred to as monitoring of air parameters. In addition, however, the monitoring can preferably also include the processing of the acquired or detected air parameters and in particular the acquired sensor signals. In this case, for example, a comparison with a threshold value or limit value can be conducted. The acquired sensor signals and/or the processed sensor signals, in particular the data obtained from the processing, are referred to hereinbelow also as the monitoring result. According to the invention, the setting of air parameters includes at least the output of at least one monitoring result. The parameters can be set automatically and/or by the user of the monitoring system. According to the invention, the setting of the air parameters can therefore entail the display of a monitoring result or another output of one or more monitoring results. In addition or alternatively, in particular devices or units which influence the air parameters directly or indirectly can be operated or actuated for setting purposes. Said devices or units can be in particular house automation devices or house automation units, which are referred to hereinbelow as house automation devices. House automation devices can be for example air influencing units, such as for example filters, windows or doors, as well as air conveying devices, such as fume extractor hoods or ventilation boxes. Moreover, the house automation devices can also be temperature regulating units, such as a heating or air conditioning system. Finally, the setting of the air parameters can also include the activation of warning mechanisms on the basis of the monitoring results. The activation of warning mechanisms can include for example the issuing of an emergency call or the triggering of an alarm.

The room in which according to the invention the air parameters are monitored and set is, according to the invention, a room in a building, in particular a living room. Although reference is made in the following to a single room, the invention is not limited thereto. Rather, it is also possible for the air parameters to be monitored and set simultaneously in a plurality of rooms of a building. The statements made in relation to one room therefore also apply analogously to a plurality of rooms.

According to the invention, the monitoring system includes at least one sensor. The sensor can constitute a temperature sensor and/or an air composition sensor. The sensor acquires air parameters and preferably outputs sensor signals which correspond to the air parameters or can be assigned to the latter, i.e. can be determined from the sensor signals. Values determined from the sensor signals are also referred to hereinbelow as sensor data. In addition to the values from the sensor signals, sensor data can in this case also contain information about the sensor itself. This information can include for example the type and/or position of the sensor, as well as ambient conditions of the sensor where appropriate. The operation of an air conveying device and/or a heat generating device, such as a stove for example, may be cited as examples of ambient conditions.

In addition, the monitoring system according to the present invention includes at least one monitoring unit which is provided separately from the sensor. Provided separately, according to the invention, describes a monitoring unit which preferably is provided arranged at a distance from the sensor and which can be operated separately from the sensor. In particular there is preferably no proprietary connection between the sensor and the monitoring unit. Such proprietary connections are used in the prior art for example for remote controls or central units for devices and allow only specific data or signals to be transmitted to a specific recipient via a specified mode of communication.

According to the invention, in contrast, the sensor is connected to the at least one monitoring unit via a wireless communications link of a communications network. A communications network, within the meaning of the invention, signifies in particular a local wireless communications network, a mobile communications network, an intranet and/or the internet. According to the invention, the communications link from the sensor to the monitoring unit is wireless. This means that the transmission of sensor signals and/or sensor data, in particular of values that have been determined from the sensor signals, takes place without a direct physical connection between the sensor and the monitoring unit. For example, the wireless communications link between the sensor and the monitoring unit can be established by way of a WLAN (Wireless Local Area Network), with the internet being included where appropriate.

Finally, the monitoring system according to the present invention comprises at least one mobile terminal device of the communications network, via which device the sensor can communicate with the monitoring unit. The mobile terminal device preferably represents a portable computer, for example a tablet PC or a mobile telephone having computer functionalities, in particular a smartphone. According to the invention, at least one part of the monitoring unit is provided on the mobile terminal device. According to the invention, the monitoring unit can therefore be provided completely or partially on the mobile terminal device. It is therefore possible according to the invention for the part of the monitoring unit that is provided on the mobile terminal device to communicate with other parts of the monitoring unit, which may be provided for example on a server on the internet, in order to enable the air parameters to be monitored and set. Preferably at least that part of the monitoring unit which serves for outputting and further processing monitoring results, for activating warning mechanisms and/or for actuating house automation devices is provided on the mobile terminal device.

A series of advantages can be achieved owing to the fact that, in the monitoring system according to the invention, the location at which the air parameters are acquired is separate from the location at which the acquired signals, data or values are processed, yet this information is transmitted over a communications network and at least one mobile terminal device is provided at which at least a part of the monitoring unit is provided. Firstly, the processing can be performed in a component of the monitoring system that does not necessarily need to be provided at the location at which the air parameters are acquired. This means that on the one hand a flexible arrangement of the sensors for acquisition of the air parameters can be realized. On the other hand the data can be processed, if necessary along with further available data, on another component of the monitoring system or a further unit of the communications system, such as a network server for example. In addition, the acquired sensor signals or sensor data, also referred to hereinbelow as signals or data, can be transmitted to different recipients in a flexible manner, since the transmission takes place over a communications network which is not restricted to a communication of the sensor with the monitoring unit. Thanks to the use of such a wireless communications network it is also easily possible to take account of further information in the processing of the sensor signals or data. Finally, through the use of such a communications network and the provision of at least one part of the monitoring unit on a mobile terminal device of the communications network, further functions of the mobile terminal device, such as the display or setup of a communications link for example, can also advantageously be used.

According to a preferred embodiment variant, the monitoring unit constitutes an application which can be executed on an electronic device alongside other programs. The application is also referred to hereinbelow as an app. The application therefore represents in particular a program which is installed on an electronic device and can be executed on the electronic device in addition to other programs. Accordingly, the application does not constitute the only program which can be executed on the electronic device. Particularly preferably, the application is designed so as to permit access to further functions of the electronic device, in particular the reception of data from a communications interface of the electronic device. In this case the electronic device preferably represents a mobile terminal device of the communications network. In particular the application therefore preferably constitutes a smartphone app or a tablet PC app.

Because the application represents an app, the monitoring system can be implemented in a flexible manner, since said app can be loaded onto an arbitrary mobile terminal device of the communications network and be installed there. This makes it possible to provide the application also on a mobile terminal device via which for example communications links to further units of the communications network can be established; a call can be initiated, for example. From the app, it is furthermore possible also to access information that may be stored, not in the mobile terminal device, but on a network server for example. This enables even greater precision to be achieved in the monitoring and setting of the air parameters.

According to an embodiment variant, the communications link between the sensor and the monitoring unit includes at least one communications interface connected to the sensor. The communications interface is preferably provided on the same device or the same component of the monitoring system on which the sensor is provided. According to the invention it is also possible for the communications interface to be combined with the sensor, which is to say that the latter has a communications interface. Since the data and/or signals are transmitted from the sensor to the communications interface over a connection that is preferably hardwired or circuit-based, it is also possible to transmit signals or data containing a high data volume to the communications interface. At the communications interface, the data or signals can then be adapted for transmission over the wireless communications network, compressed or converted for example. It is advantageous, in particular in the case of a communications interface which is not integrated into the sensor, if said communications interface is able to serve as a means of transmission for a plurality of sensors, in other words if it can be connected to a plurality of sensors. In this case it is also possible to use as the communications interface an interface which is already provided for other purposes, i.e. for transmitting other data, on a device or an appliance on which the sensor or sensors are disposed.

The monitoring unit is preferably configured for processing signal data. According to the invention, the processing of signal data preferably entails the generation of monitoring results. This can include assigning values to acquired sensor signals on the one hand and, on the other, comparing acquired or determined values or sensor data with predefined values. The comparison with predefined values can entail the comparison with a threshold value, which can also be referred to as a limit value, from which the reaching or exceeding of the threshold value is then obtained as the monitoring result. In addition or alternatively, the comparison with predefined values can also lead to data being read out from a database. For example, if a specific particle size is detected in the air, it can be identified with reference to a database which types of pollen will be prevalent at the given time of year.

According to an embodiment variant, the monitoring unit comprises at least one control unit for actuating at least one house automation device, in particular an air influencing unit or air conveying device and/or a control unit for activating warning mechanisms and/or at least one output unit for outputting, in particular for displaying, monitoring results.

The control unit(s) and the output unit are preferably realized as subprograms in the application. The control unit(s) and the output unit can be combined in a common unit. What is understood as a control unit, according to the invention, is that part of the monitoring unit, which can also be embodied as a subprogram of the application, by means of which further components of the monitoring unit and/or external units or devices can be actuated and/or activated. In particular the control unit can be a subprogram of the application by means of which monitoring results are converted into such a format that they can be output on an output device. Thus, for example, the values or sensor data determined from the acquired sensor signals can be displayed or an exceeding of a threshold value can be displayed. Furthermore, the control unit can also actuate or activate a different application on the mobile terminal device. Thus, for example, an emergency call can be issued upon detection of a threshold value being exceeded. Moreover, it is also possible for the control unit of the monitoring unit to actuate an external device. For example, an automatic window opener can be actuated if the carbon monoxide content of the air exceeds a certain threshold value. Alternatively or in addition, it is also possible for an air conditioning system to be actuated by the control unit of the monitoring unit if the temperature exceeds a threshold value.

According to a preferred embodiment variant, at least one sensor is provided on an air conveying device. An air conveying device, within the meaning of the present invention, signifies a device by means of which an airflow can be generated in the room and in particular air can be aspirated to a specific location. According to an embodiment variant, the air conveying device constitutes a fume extraction hood. However, it is also possible to use for example a ventilation conduit or an air conditioning system as an air conveying device.

Because the sensor is provided on the air conveying device, the air parameters can reliably be determined for the air from the entire room, since the air is aspirated to the air conveying device. Furthermore, by arranging the sensor on the air conveying device it is possible to prevent the undesirable acquisition of peaks of an air parameter.

According to a further aspect, the object is achieved according to the present invention by means of a fume extraction device which is characterized in that the fume extraction device comprises at least one sensor and at least one communications interface for communicating with the at least one terminal device, in that the communications interface for communicating with the at least one terminal device is a wireless communications interface, the terminal device is a terminal device of a communications network and there is provided in the terminal device at least one monitoring unit in the form of an application, to which at least sensor data of the at least one sensor can be transmitted from the fume extraction device.

By a fume extraction device, within the meaning of the invention, is to be understood an air conveying device and in particular a device for aspirating and preferably for cleaning air. Particularly preferably, the fume extraction device represents a household appliance designed for operation in a kitchen, in particular for evacuating fumes and vapors from a stove top or countertop. This embodiment variant of the fume extraction device is also referred to as a fume extraction hood. According to the invention the fume extraction device comprises at least one sensor. In this case the sensor can be provided on or in the fume extraction device. Preferably the sensor or sensors are provided in a section of the fume extraction device in which the aspiration flow generated by the fan of the fume extraction device acts on the airflow in and/or on the fume extraction device. In particular the sensor can therefore be disposed for example in a section of the fume extraction device at which the airflow which is conducted to the intake aperture of the fume extraction device flows or in the section in which the airflow is conducted from the intake aperture to the fan of the fume extraction device. If a grease filter is provided on the fume extraction device, the sensor is preferably disposed upstream of the grease filter in the flow direction if the sensor is a pollen sensor. In the case of a temperature sensor or another air composition sensor the sensor can also be disposed downstream of the grease filter in the flow direction.

The fume extraction device according to the invention also includes at least one interface for communicating with at least one terminal device, in particular a mobile terminal device of the communications network. According to the invention the interface is also referred to as a communications interface. The interface is designed in particular for transmitting signals and/or data. The interface can be integrated together with one or more sensors in one unit or be connected to the sensor or sensors. In particular signals can be received by the sensor or sensors via the interface. The interface can also serve for processing the received signals. The signals can represent sensor signals which reflect a condition detected by the sensor. In addition or alternatively, sensor data, such as information relating to the sensor and/or a value determined from sensor signals for example, can also be acquired by the sensor. In the interface the signals are processed at least in such a way that they can be transmitted to a component of the monitoring system that is external to the fume extraction device. The interface preferably has at least one transmit unit. According to the invention the interface is a wireless interface. A wireless interface refers in particular to a radio interface from which signals can be transmitted by radio to a component of the monitoring system that is separate from the fume extraction hood.

According to the invention, the terminal device constitutes a terminal device of a communications network which has already been described hereinabove with reference to the inventive monitoring system. The further features of the preferred embodiment variant of the fume extraction device have also already been described hereinabove with reference to the monitoring system.

The use of a fume extraction device in the monitoring system according to the invention is associated with a series of advantages. In particular a fume extraction device, in particular a fume extraction hood, is normally already provided in a kitchen. The sensor and the communications interface can therefore be provided on a device that is already present. Furthermore, air from the room is aspirated by a fume extraction device and the air parameters acquired in said aspirated air are therefore representative of the entire room.

According to an embodiment variant, the at least one sensor on the fume extraction device is a sensor for acquiring at least one secondary air parameter of the fume extraction device. The term secondary air parameters serves to describe such air parameters that are not taken into account or, as the case may be, are not necessary for the operation of the fume extraction device and in particular a fume extraction hood. During the operation of a fume extraction device, in particular a fume extraction hood, it is already known for example to determine the grease content in the aspirated air and by that means to adjust for example the fan speed accordingly. According to the invention, this air parameter is referred to as the primary air parameter of the fume extraction device, since this is required for the proper operation or optimized operation of the fume extraction device. In contrast, the secondary air parameters, such as the pollen content, for example, or the content in terms of harmful gaseous substances, are not required for the operation of the fume extraction device. Since at least one sensor for secondary air parameters is provided in the fume extraction device according to the invention, said sensor can be set independently of the primary air parameters required for the operation of the fume extraction device. In particular the sensitivity of the sensor for example can be set such that the air parameters for the inventive monitoring and adjustment of the air parameters can be reliably acquired without detrimentally affecting the operation of the fume extraction device.

According to an embodiment variant, the at least one communications interface on the fume extraction device is connected to the sensor or to at least one of the sensors. This embodiment variant is of particular advantage in a fume extraction device, since by this means it is possible to use for the transmission of sensor data a communications interface which may already be provided for other purposes on the fume extraction device. As a result this reduces the complexity of the fume extraction device compared with a fume extraction device on which sensors having their own dedicated communications interfaces are provided.

According to a preferred embodiment variant, the sensor on the fume extraction device can be operated independently of the fume extraction device. This has the advantage that air parameters can be acquired even when the fume extraction device is switched off and consequently even during idle periods of the fume extraction device monitoring results can if necessary be made available to the user of the monitoring system or suitable measures can be initiated.

According to a further aspect, the present invention relates to a method for monitoring and setting air parameters in a room. The method is characterized in that the method is performed by means of a monitoring system according to the invention and preferably by means of a fume extraction device according to the invention.

Preferably the method comprises the acquisition of at least one air parameter at a sensor, the transmission of sensor data to at least one monitoring unit over a communications network, and processing of the sensor data at the monitoring unit as well as transmission of the monitoring results thus obtained to an output unit and/or to a control unit.

Advantages and features described in relation to the monitoring system according to the invention are valid—insofar as applicable—analogously for the fume extraction device according to the invention and the method according to the invention, and vice versa in each case.

BRIEF DESCRIPTION OF THE DRAWINGS

The invention is described again in more precise detail hereinbelow with reference to the attached figures, in which.

DETAILED DESCRIPTION OF EXEMPLARY EMBODIMENTS OF THE PRESENT INVENTION

Figure 1:
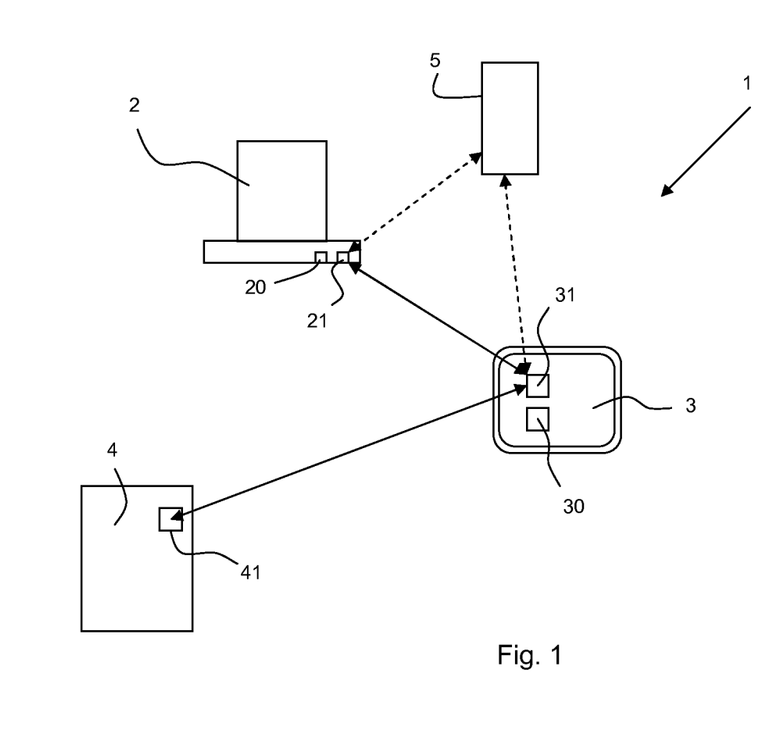
FIG. 1: shows a schematic representation of an embodiment variant of a monitoring system with fume extraction device.

FIG. 1 shows a schematic representation of an embodiment variant of the monitoring system 1 according to the invention. In the embodiment variant shown, the monitoring system 1 comprises a fume extraction device 2, also referred to hereinbelow as a fume extraction hood 2, a house automation device 4, and a terminal device 3. Also depicted schematically is a server 5 of the communications network, representing a network server for example.

In the embodiment variant shown, a sensor 20 is provided on the fume extraction hood 2. It is, however, also possible for more than one sensor 20 to be provided on the fume extraction hood 2. The sensor 20 can be provided in the interior of the fume extraction hood 2, in particular close to the fan (not shown) of the fume extraction hood 2. Alternatively, however, the sensor 20 can also be provided on the exterior of the fume extraction hood 2, for example on the canopy of the fume extraction hood 2. In this arrangement too, however, the sensor 20 is preferably provided in proximity to the intake aperture of the fume extraction hood 2. The fume extraction hood 2 additionally includes an interface 21. The interface 21 constitutes a communications interface and in particular a radio interface. The interface 21 preferably comprises a transmit unit and where appropriate a receive unit connected to or integrated in the transmit unit. The interface 21 can therefore comprise what is known as a transceiver unit. In the embodiment variant illustrated, the interface 21 is shown separately from the sensor 20, though it also falls within the scope of the invention for the interface 21 to be integrated in the sensor 20.

The home automation device 4 can be for example a device for controlling windows, doors or blinds, or a security or safety device, such as an intrusion monitoring device or fire alarm. The home automation device 4 has an interface 41 which represents a communications interface, in particular a radio interface, and can correspond to the interface 21 of the fume extraction hood 2.

The terminal device 3 can be for example a mobile telephone, in particular a smartphone or a tablet PC. At least a part of a monitoring unit 30 is provided in the terminal device 3. Said monitoring unit 30 preferably constitutes a program that is installed on the terminal device and can be executed there. The monitoring unit 30 can therefore represent a software program for example, in particular a so-called app. The terminal device 3 further comprises an interface 31 which represents a communications interface, in particular a radio interface, and can correspond to the interface 21 of the fume extraction hood 2. Finally there is provided on the terminal device 3 an output device 32 which in the embodiment variant shown represents a visualization unit in the form of a display. The interface 31 is preferably connected to the monitoring unit 30 for the purpose of transmitting data.

Figure 2:
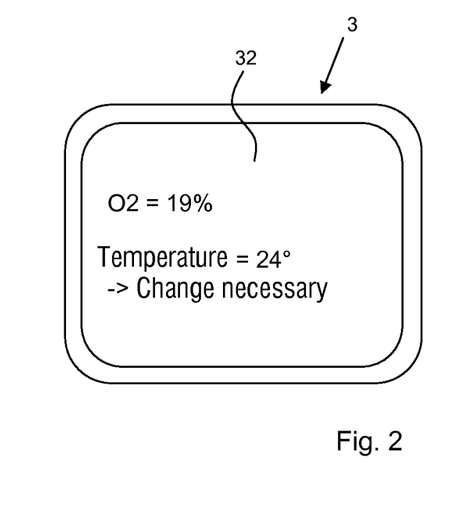
FIG. 2: shows a schematic representation of a terminal device of an embodiment variant of the monitoring system according to the invention.

The mode of operation of the fume extraction hood 2 and the monitoring system 1 shall be explained again hereinbelow with reference to the figures. The sensor 20 on the fume extraction hood 2 acquires air parameters, such as the temperature, the relative humidity of the air, for example, and/or parameters relating to the composition of the air, such as a content in terms of solid or gaseous substances, for example. Solid substances in this context can be pollen or dust, for example, while gaseous substances can be for example CO, CO2, SO2 or NOx. The sensor signals acquired at the sensor 20 are processed preferably at the sensor 20 itself or in the interface 21 to yield values which can also be referred to as sensor data. In addition, other sensor data, such as information concerning the position of the sensor, for example, or ambient conditions of the sensor 20, can also be transmitted to the interface 21 along with the values determined from the sensor signals. The sensor data can then be transmitted wirelessly to the terminal device 3 via the interface 21 of the fume extraction hood 2. The sensor data thus transmitted is received at the interface 31 of the terminal device 3. From there, the sensor data is transmitted to the monitoring unit 30. The sensor data is preferably processed in the monitoring unit 30. This can entail for example conducting a comparison of received sensor data with predefined threshold values or limit values. Alternatively or in addition, the sensor data can be converted into a format in which it can be output, in the currently illustrated case displayed, via the output device 32. At the same time as the output of the sensor data, monitoring results can additionally be output as well. In particular, as shown in FIG. 2, it can be output, i.e. displayed, that a change is necessary if it is detected that one or more threshold values have been exceeded.

In addition to said data transmission from the fume extraction hood 2 to the terminal device 3, information can also be transmitted to the terminal device 3 from the home automation device 4 via the interface 41. Said information can be for example the degree of opening of a window, the setting of an air conditioning system, and the like.

The information thus received at the interface 31 of the terminal device 3 can be taken into account during the processing of the sensor data of the sensor 20.

Figure 3:
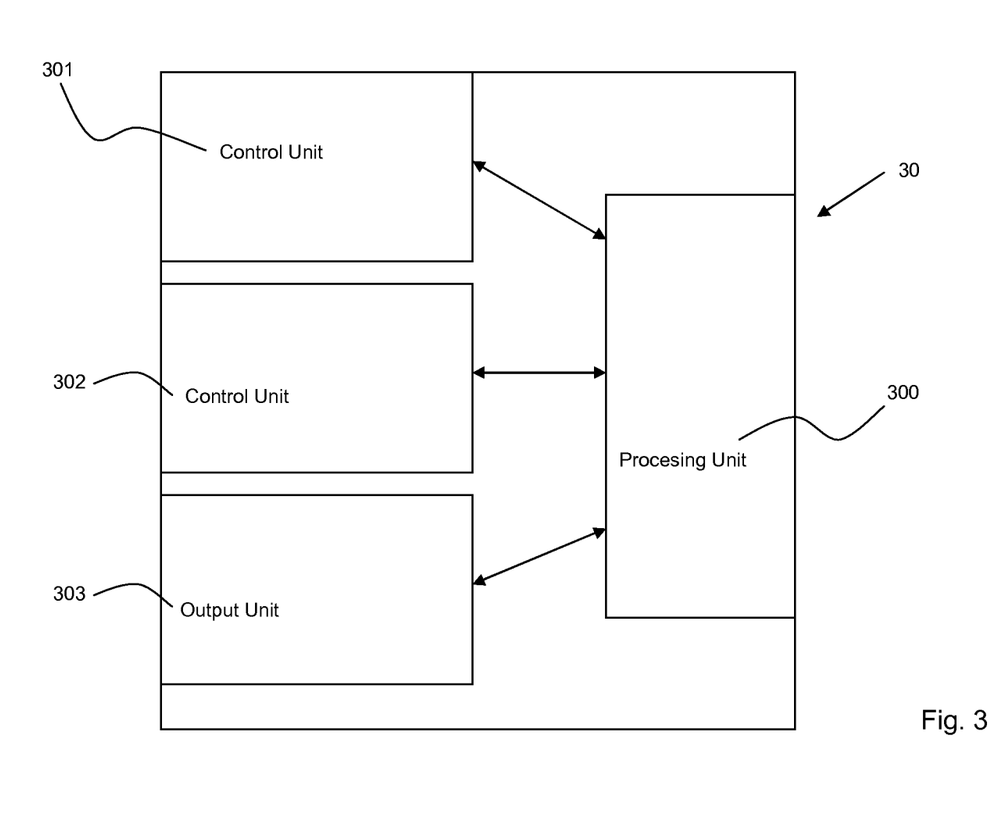
FIG. 3: shows a schematic representation of an embodiment variant of the monitoring unit.

As can be seen from FIG. 3, the monitoring unit 30 can be composed of a plurality of parts, though at least some of these can also be combined. In the embodiment variant shown, the monitoring unit 30 comprises a processing unit 300, a control unit 301 for actuating at least one air influencing unit, a control unit 302 for activating warning mechanisms, and an output unit 303 for outputting monitoring results.

The processing unit 300 is preferably connected to the interface 31 of the mobile terminal device 3. In the embodiment variant shown, the processing unit 300 is provided on the terminal device 3. It is, however, also possible for the processing unit 300 to be provided for example on the server 5 or on another component of the monitoring system 1 and to communicate solely with the other parts of the monitoring unit 30 on the mobile terminal device 3. For example, a comparison of received sensor data, in particular of values that have been determined from sensor signals, with one or more threshold or limit values can be performed in the processing unit. Depending on the result of the comparison, which can be referred to as the monitoring result, one of the other units of the monitoring unit 30 can be actuated. For example, if a predefined temperature value is exceeded, the control unit 301 can be prompted to actuate at least one air influencing unit or an air conveying device. As a result thereof, a corresponding signal can be transmitted by the monitoring unit 30, in particular via the interface 31, to the corresponding home automation device 4 and for example the heating for the room in which the air parameters were acquired can be turned down. In addition or alternatively, the output unit 303 can be actuated in order to output monitoring results. By this means an output, for example a display on the output device 32, can be generated from which it is made evident to the user of the monitoring system 1 that the heating must be turned down or is currently being turned down. Furthermore, the control unit 302, which serves for activating warning mechanisms, can be actuated by the processing unit 300, for example. This can take place for example if it is detected that a pollen concentration in the air has been exceeded. In this case, the communications unit (not shown) of the mobile terminal device 3 can for example be activated by way of the control unit 302 and an emergency call sent, for example, to the treating physician. Furthermore, it is of course also possible for the control units 301, 302 and the output unit 303 to be interconnected in such a way that they can activate or actuate one another.

As represented schematically in FIG. 2, sensor data can also be transmitted from the interface 21 of the fume extraction device 2 to the mobile terminal device 5 by way of the server 5. In this case the sensor data is preferably transmitted to the server 5, on which it is processed in a processing unit 300 of the monitoring unit 30. The thus processed sensor data or the monitoring results obtained therefrom can then be transmitted to the corresponding units 301, 302, 303 on the mobile terminal device 3. In the provision of the processing of the sensor data on the server 5 it is also possible to take account in a simple manner of additional information, such as details of the time of year or the outside temperature for example, during the processing and selection of the unit 301, 302, 303 that is to be actuated. Also when the processing unit 300 is provided on the mobile terminal device 3 itself, such information or other information, such as personal profiles of the user of the monitoring system 1 for example, can be taken into account.

The present invention is not limited to the illustrated embodiment variants and examples. Preferred embodiment variants of the invention can be summarized as follows. According to one embodiment variant, the integration of sensors into fume extraction hoods for the purpose of analyzing air parameters such as temperature, air humidity, pollen and gaseous substances is made possible by means of the present invention. The acquired parameters are preferably evaluated by means of a corresponding app, on a smartphone or tablet PC for example.

A number of advantages can be achieved by means of the present invention. Living room air quality has a major influence on the wellbeing and productivity of human beings. Furthermore, an analysis of the composition of the air provides inferences concerning harmful gases and substances that constitute an impediment or hazard to allergy sufferers. In addition, room temperature and air humidity are also contributory factors in the energy requirements in private households and should therefore be set in an optimized manner under the aspect of energy efficiency.

According to an embodiment variant of the invention, at least one sensor is integrated into a fume extraction hood for the purpose of acquiring a variety of air parameters such as temperature, air humidity, pollen and gaseous substances ($CO_2$, CO, $SO_2$, NOx, etc.). In this case the fume extraction hood together with sensor can represent part of a larger monitoring system which can also be referred to as the overall system. House automation technology (windows, doors, blinds) or security or safety devices (alarm annunciators for intrusion, fire) can also be integrated in the monitoring system. The sensor on the fume extraction hood acquires the air values during operation of the fume extraction hood and also when it is not in operation. In the first case more comprehensive results can be concluded, since air masses from the entire living room are aspirated. The sensor has for example a radio interface or is connected to such an interface and passes on the acquired values to a special app or software on a smartphone. The app/software evaluates the data and gives the user feedback on the air composition and advice on possible improvement.

By means of the present invention it is possible to achieve the following advantages, among others. In particular the present invention constitutes a space-saving solution, since because the sensor is integrated into the fume extraction housing no separate space is required in the living room. The analysis of the air aspirated by the fume extraction hood yields qualitatively higher-value results than the analysis of stationary air. Mold can also be avoided since an optimal air composition can be set. The level of safety and security in living quarters is also increased. An emergency call can be made automatically via the app in the event of smoke or fumes being detected. In addition, quality of life is enhanced by virtue of better air in the living room. The present invention can also serve as an aid to allergy sufferers, such as hayfever sufferers, or asthmatics. Energy savings can be achieved thanks to the optimal living room temperature. Additional advantages can furthermore be derived as a result of the integration into other systems in the household, such as security and safety (motion detectors, fire alarms, etc.).

What is claimed is:

1. A monitoring system for monitoring and setting an air parameter in a room, said monitoring system comprising:
   a fume extraction hood for a household cooking appliance,
   a sensor provided on the fume extraction hood and the sensor is configured for operation independently of the fume extraction hood when the fume extraction hood is switched off,
   a monitoring unit, which is provided separately from the sensor;
   a communication network having a wireless communication link; which connects the monitoring unit to the sensor, and
   a mobile terminal device on which a part of the monitoring unit is provided, wherein the monitoring unit includes a control unit provided separately from the sensor and in communication with the sensor, the control unit configured to process a signal received from the sensor, the control unit in communication with at least one home automation device that is remote from the sensor and the monitoring unit and configured to transmit a control signal to the at least one home automation device to actuate the at least one home automation device based on the processed signal.

2. The monitoring system of claim 1, wherein the monitoring unit is configured as an application for execution on an electronic device.

3. The monitoring system of claim 1, wherein the communication link between the sensor and the monitoring unit comprises at least one communication interface connected to the sensor.

4. The monitoring system of claim 1, wherein the monitoring unit has a processing unit for processing signal data.

5. The monitoring system of claim 1, wherein the monitoring unit is arranged at a distance from the sensor and configured to be operated separately from the sensor and the at least one home automation device.

6. The monitoring system of claim 1, wherein the sensor is configured to acquire the air parameter in the room at a location that is separate from, and at a distance from, the location of the control unit where the signal received from the sensor is processed.

7. The monitoring system of claim 1, wherein the fume extraction hood includes an air influencing unit.

8. The monitoring system of claim 1, wherein the fume extraction hood is an aft conveying device, said sensor being provided on the air conveying device.

9. The monitoring system of claim 6, wherein the sensor is configured to acquire the air parameter from air being aspirated by the air conveying device, and
   wherein the air conveying device is at a location that is separate from, and at a distance from, the location of the control unit where the signal received from the sensor is processed.

10. The monitoring system of claim 8, wherein the air conveying device includes one of a ventilation conduit and an air conditioning system.

11. The monitoring system of claim 1, wherein the sensor is configured to acquire the air parameter in the room at a location that is separate from, and at a distance from, the location of the control unit,
    wherein the signal received by the control unit from the sensor represents the air parameter acquired by the sensor, and
    wherein the control unit is configured to process the signal received from the sensor to provide a monitoring result.

12. The monitoring system of claim 11, wherein the control unit is configured to automatically transmit a control signal to the at least one home automation device to automatically actuate the at least one home automation device based on the monitoring result.

13. The monitoring system of claim 11, wherein the at least one home automation device includes a warning mechanism in communication with the control unit,
    wherein the control unit is configured to actuate the warning mechanism based on the monitoring result.

14. A fume extraction hood for a household cooking appliance, comprising:
    a sensor provided on the fume extraction hood and the sensor is configured for operation independently of the fume extraction hood when the fume extraction hood is switched off, and
    a communication interface configured as a wireless communication interface for communicating with a terminal device of a communication network of a monitoring system configured for monitoring and setting an aft parameter in a room and having a monitoring unit, which is remote from the sensor, the monitoring unit configured to receive sensor data of the sensor, and wherein the monitoring system includes a control unit, which is remote from the sensor, configured to process the sensor data received from the sensor, the control unit in communication with at least one home automation device that is remote from the sensor and monitoring unit and configured to transmit a control signal to the at least one home automation device to actuate the at least one home automation device based on the processed sensor data.

15. The fume extraction hood of claim 14, wherein the sensor is configured for acquiring a secondary air parameter of the fume extraction hood.

16. The fume extraction hood of claim 14, wherein the communication interface is connected to the sensor.

17. A method, comprising:
providing a sensor on a fume extraction hood for a household cooking appliance and the sensor is configured for operation independently of the fume extraction hood when the fume extraction hood is switched off;
determining an air parameter in a room to produce a sensor signal from the sensor;
processing the sensor signal to sensor data;
transmitting the sensor data by a wireless communication link to a terminal device;
transmitting the sensor data from the terminal device to a monitoring unit, which is remote from the sensor and which processes the sensor data; and
transmitting a control signal from the monitoring unit to at least one home automation device that is remote from the sensor and the monitoring unit.

18. The method of claim 17, further comprising configuring the monitoring unit as an application for execution on an electronic device.

19. The method of claim 17, executed by the fume extraction hood having the sensor to determine the air parameter and to process the sensor signal to the sensor data, and a communication interface configured as the wireless communication interface for communicating with the terminal device.

20. A monitoring system for monitoring and setting an aft parameter in a room, said monitoring system comprising:
a fume extraction hood for a household cooking appliance configured to aspirate aft from the room based on a primary aft parameter required for optimized operation of the fume extraction hood, the fume extraction hood having a sensor configured for acquiring a secondary air parameter not required for the optimized operation of the fume extraction hood; and the sensor is configured for operation independently of the fume extraction hood when the fume extraction hood is switched off;
a mobile terminal device including at least a part of a monitoring unit, which is provided separately from the fume extraction hood; and
a communication network having a wireless communication link, which connects the monitoring unit to the sensor of the fume extraction hood,
wherein the monitoring unit includes a control unit provided separately from the fume extraction hood and configured to process a signal received from the sensor based on the secondary air parameter and to transmit a control signal to at least one of the fume extraction hood to actuate the fume extraction hood to aspirate air from the room based on the secondary aft parameter and to at least one home automation device to actuate the at least one home automation device based on the secondary air parameter.

* * * * *